United States Patent [19]
Abe et al.

[11] Patent Number: 4,933,277
[45] Date of Patent: Jun. 12, 1990

[54] METHOD OF QUANTITATIVE ANALYSIS OF HYDROGEN PEROXIDE AND REAGENT THEREFOR

[75] Inventors: Toshikatsu Abe; Mitsuhisa Manabe; Masayuki Nozawa; Atsushi Izumi; Fumio Masumi; Akemichi Maki, all of Tokyo, Japan

[73] Assignee: Daiichi Pure Chemicals Co., Ltd., Tokyo, Japan

[21] Appl. No.: 262,720

[22] Filed: Oct. 26, 1988

[30] Foreign Application Priority Data

Oct. 26, 1987 [JP] Japan ................................ 62-269987

[51] Int. Cl.$^5$ ...................... C12Q 1/28; G01N 33/72; C12P 7/62
[52] U.S. Cl. ..................................... 435/28; 435/810; 436/135; 436/84; 436/66; 436/164
[58] Field of Search ...................... 435/25, 27, 28, 810; 436/66, 135, 164, 84

[56] References Cited

FOREIGN PATENT DOCUMENTS 195559 8/1987 Japan .
433394 9/1974 U.S.S.R. .

OTHER PUBLICATIONS

Yandell et al, Biochim. Biophys. Acta, 748: 263–270 "Steady-State Kinetics of Yeast Cytochrome c Peroxidase Catalyzed Oxidation of Inorganic Reductants by Hydrogen Peroxide", (1983).
Wada et al, Chemical Abstracts, 98: 227135v, p. 736 (1983).
Kina, "The Molecular Design of Highly Sensitive Photometric Reagent (1)", Dojin New, 39, 8–10, 1987.
Horiguchi, et al. "Water Soluble Pyridylazoaminophenols and Pyridylazo Amino Benzoic Acids as Highly Sensitive Photometric Reagents for zinc, uranium, cobalt and nickel."
Katami et al, "Spectrophotometric Determination of Cobalt in Pepperbush Leaves and Coal Fly Ashes Using 2-(2-Benzothiazolylazo)-5-Dimethylaminbenzoic Acid", Prefect. Res Inst. Environ. Pollut, 110(4), pp. 399–401.
Wada et al., "Spectrophotometric Determination of Cobalt in Steel with 2-(2-Thiazolylazo)-4-methyl-5-(-Sulfomethylamino)Benzoic Acid (TAMSMB)", Mikrochim. Acta, 2(1–2), pp. 139–149, 1983.
Wada et al, "2-(2-Thiazolylazo)-4-Methyl-5-(Sulfomethylamino)Benzoic Acid as a Reagent for the Spectrophotometric Determination of Cobalt", Anal. Chim. Acta. (1982), 135(2), pp. 333–341.

Primary Examiner—Esther M. Kepplinger
Attorney, Agent, or Firm—Oblon, Spivak, McClelland, Maier & Neustadt

[57] ABSTRACT

A method for quantitative analysis of hydrogen peroxide at a high precision is disclosed. The method comprises reacting a divalent cobalt compound with hydrogen peroxide in the presence of peroxidase or a substance similar to peroxidase to produce a trivalent cobalt compound, reacting the trivalent cobalt compound thus produced with a trivalent cobalt indicator to produced a colored complex, and subjecting the colored complex to colorimetric quantitative analysis. The method enables various enzymatic activities producing hydrogen peroxide by the reaction with substrates as well as the amount or activity of substances involving the known enzymatic reactions linked with such enzymatic reactions, of enzymes and coenzymes, to be quantitatively determined very easily at a high sensitivity at a wavelength of above 600 nm without the interference of hemoglobin, bilirubin, or turbidity.

4 Claims, No Drawings

METHOD OF QUANTITATIVE ANALYSIS OF HYDROGEN PEROXIDE AND REAGENT THEREFOR

BACKGROUND OF THE INVENTION

1. Field of the Invention

This invention relates to a method for quantitative analysis of hydrogen peroxide and a regent for use in such a quantitative analysis.

2. Description of the Background

Measuring components contained in body fluids such as blood and urine has become very important in recent years for the diagnosis of diseases, and determination of curing effects and cause of diseases.

Among various methods for measuring body fluid components heretofore developed and adopted, quantitative analyses of hydrogen peroxide are widely used and have become very important. A commonly accepted quantitative analysis of hydrogen peroxide comprises reacting a suitable oxidase with a component to be analyzed, producing hydrogen peroxide of the amount corresponding to the amount of the component to be analyzed contained in the sample, having a reagent for the analysis of hydrogen peroxide colored, and then carrying out the colorimetric analysis to determine the amount of said component. This method is utilized for the quantitative analysis of cholesterol, neutral fat, glucose, phospholipid, free fatty acid, uric acid, inorganic phosphorous compounds, pyrbic acid, L-lactic acid, amino acids, and the like, contained, for example, in blood or urine. The method is also applied to the quantitative analysis of enzymatic activities, including activities of choline esterase, α-amylase, monoamine oxidase, transaminase, or the like.

A coloring reagent generally used for the quantitative analysis of hydrogen peroxide is a combination of 4-aminoantipyrine and phenol, aniline, toluidine, anisidine, or derivatives of these compounds [for instance, *Biochemistry*, 6, 24–27 (1969)]. Oxidative condensates produced through such a combination of compounds, however, have a rather short maximum absorbance wavelength (λmax), e.g. in the neighborhood of 500 nm, and for this reason they are liable to be affected by colored substances commonly existing in a body fluid such as hemoglobin, bilirubin, or the like. They are also largely affected by the turbidity. In addition, their sensitivity was low, so that the method was not effective for the analysis of a component which is contained in a sample at a very small amount.

The present inventors have conducted extensive studies for the development of a quantitative analysis overcoming these problems, and as a result found that the combined use of a divalent cobalt compound and a trivalent cobalt indicator can provide a highly sensitive quantitative analysis of hydrogen peroxide at a wavelength greater than 600 nm. Such a finding has led to the completion of this invention.

SUMMARY OF THE INVENTION

Accordingly, an object of this invention is to provide a method for quantitative analysis of hydrogen peroxide which comprises reacting a divalent cobalt compound with hydrogen peroxide in the presence of peroxidase or a substance similar to peroxidase (peroxidase and substances similar to peroxidase is hereinafter collectively referred to as "POD") to produce a trivalent cobalt compound, reacting the trivalent cobalt compound thus produced with a trivalent cobalt indicator to produced a colored complex, and subjecting the colored complex to colorimetric quantitative analysis.

More specific object of this invention is to provide the above method for quantitative analysis of hydrogen peroxide, wherein said trivalent cobalt indicator a compound represented by the following formula (I) or a salt thereof is used as a trivalent cobalt indicator:

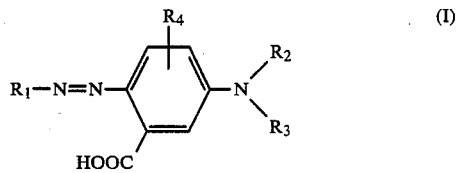

wherein $R_1$ represents

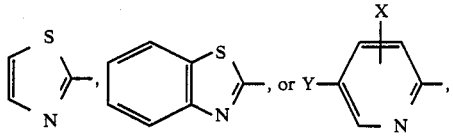

(wherein X and Y may be the same or different and represent hydrogen atoms, halogen atoms, or halogenated alkyl groups), $R_2$ and $R_3$ may be the same or different and represent hydrogen atoms, lower alkyl groups, sulfo alkyl groups, or ω-sulfohydroxy alkyl groups, and $R_4$ represents a hydrogen atom or a lower alkyl group.

Another object of this invention is to provide a reagent for the quantitative analysis of hydrogen peroxide which comprises a divalent cobalt compound, a trivalent cobalt indicator, and POD.

Other objects, features and advantages of the invention will hereinafter become more readily apparent from the following description.

DETAILED DESCRIPTION OF THE INVENTION AND PREFERRED EMBODIMENTS

The quantitative determination according to the present invention utilizes the following reaction:

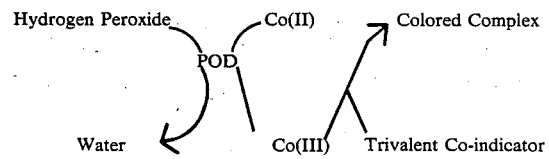

According to the above reaction scheme hydrogen peroxide which is the compound to be analyzed is reacted with a divalent cobalt compound in the presence of POD, the trivalent cobalt produced by this reaction is reacted with a trivalent cobalt indicator, and then the colored complex produced is quantitatively analyzed to determine the amount of hydrogen peroxide.

There are no specific limitations as to divalent cobalt compounds used in the analysis. Specifically, they include cobalt(II) chloride, cobalt(II) sulfate, cobalt(II) nitrate, cobalt(II) ammoniumsulfate, cobalt(II) acetate, bis(acetylacenato) cobalt(II), cobalt(II) sodium ethylenediamine, and other cobalt(II) compounds having a similar reactivity with these compounds.

There are also no specific limitations as to trivalent cobalt indicators used in the analysis of this invention, so long as such an indicator is capable of producing a colored complex by the reaction with trivalent cobalt. Given as typical examples of such a trivalent cobalt indicator are hetero-cyclic azoaminobenzoic acid derivatives represented by the following formula (I) as well as salts of such compounds:

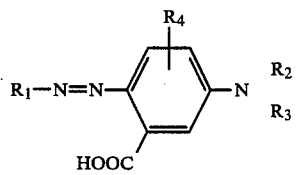
(I)

wherein $R_1$ represents

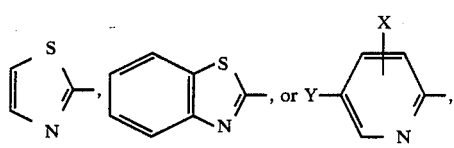

(wherein X and Y may be the same or different and represent hydrogen atoms, halogen atoms, or halogenated alkyl groups), $R_2$ and $R_3$ may be the same or different and represent hydrogen atoms, lower alkyl groups, sulfo alkyl groups, or ω-sulfohydroxy alkyl groups, and $R_4$ represents a hydrogen atom or a lower alkyl group.

More specifically, they include, by way of example, the following compounds:

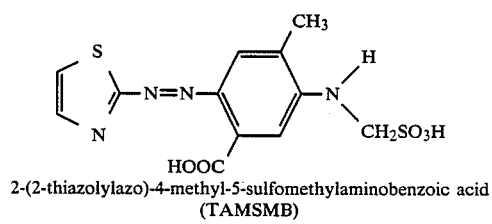
(1)
2-(2-thiazolylazo)-4-methyl-5-sulfomethylaminobenzoic acid (TAMSMB)

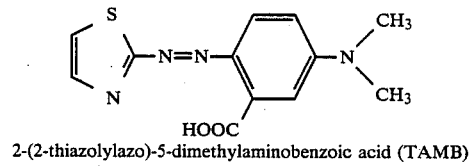
(2)
2-(2-thiazolylazo)-5-dimethylaminobenzoic acid (TAMB)

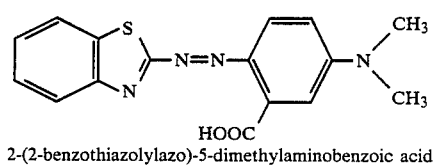
(3)
2-(2-benzothiazolylazo)-5-dimethylaminobenzoic acid (BTAMB)

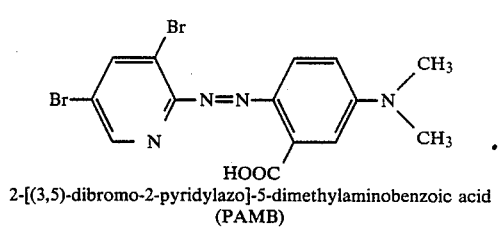
(4)
2-[(3,5)-dibromo-2-pyridylazo]-5-dimethylaminobenzoic acid (PAMB)

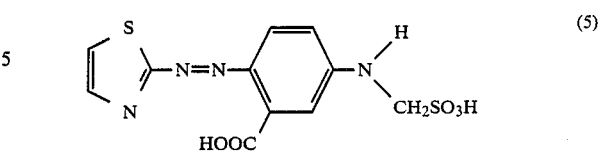
(5)
2-(2-thiazolylazo)-5-sulfomethylaminobenzoic acid (TASMB)

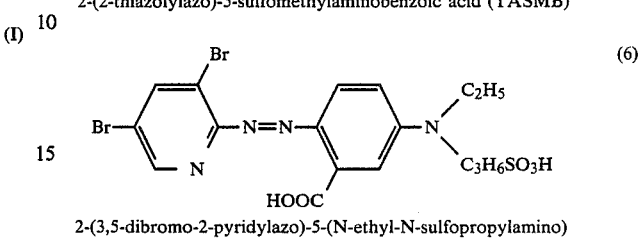
(6)
2-(3,5-dibromo-2-pyridylazo)-5-(N-ethyl-N-sulfopropylamino) benzoic acid (DSAB)

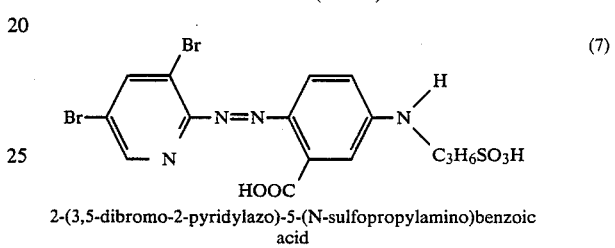
(7)
2-(3,5-dibromo-2-pyridylazo)-5-(N-sulfopropylamino)benzoic acid

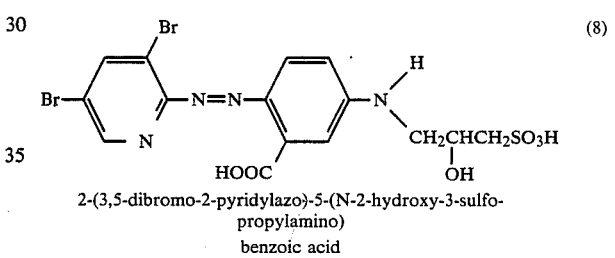
(8)
2-(3,5-dibromo-2-pyridylazo)-5-(N-2-hydroxy-3-sulfopropylamino) benzoic acid

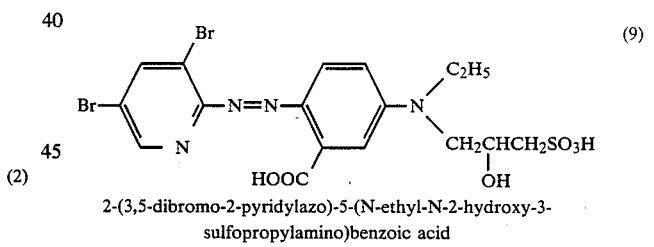
(9)
2-(3,5-dibromo-2-pyridylazo)-5-(N-ethyl-N-2-hydroxy-3-sulfopropylamino)benzoic acid

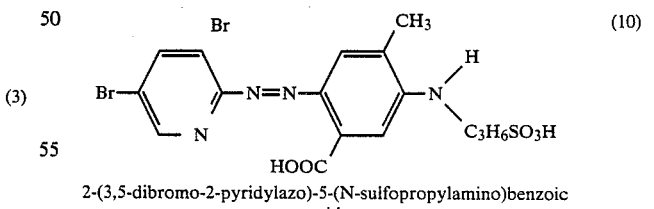
(10)
2-(3,5-dibromo-2-pyridylazo)-5-(N-sulfopropylamino)benzoic acid

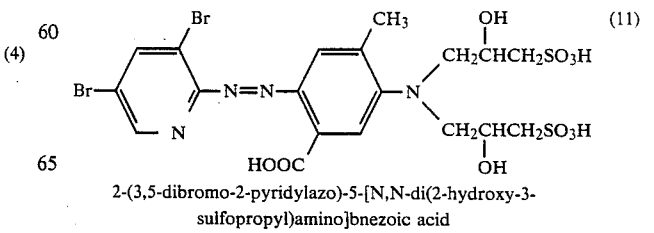
(11)
2-(3,5-dibromo-2-pyridylazo)-5-[N,N-di(2-hydroxy-3-sulfopropyl)amino]bnezoic acid

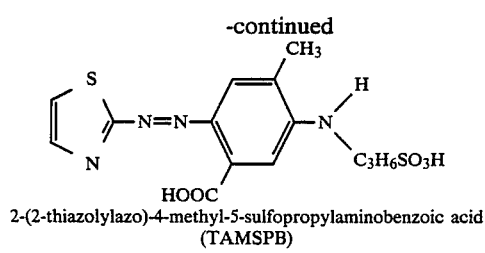

2-(2-thiazolylazo)-4-methyl-5-sulfopropylaminobenzoic acid
(TAMSPB)

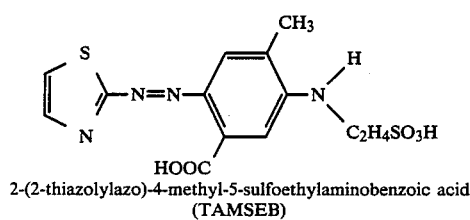

2-(2-thiazolylazo)-4-methyl-5-sulfoethylaminobenzoic acid
(TAMSEB)

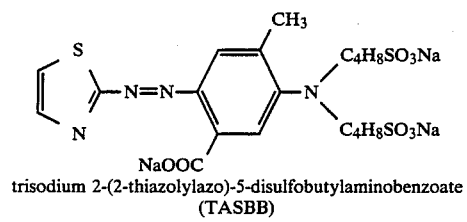

trisodium 2-(2-thiazolylazo)-5-disulfobutylaminobenzoate
(TASBB)

Of the above compounds, (1) to (4) are commercially available in the market. Compound (5) can be prepared according to the method described, for example, in *Analytical Chemistry*, 28, 535–540 (1979). Compounds (6) to (11) can be synthesized according to the method described in *Analytical Science*, 1, 461–465 (1985). Compounds (12) and (13) can be synthesized according to the method described in *Mikrochimica Acta* [Wien], 1983 III, 235–244. The method for the synthesis of compound (14) will be illustrated as an example of the preferred embodiment of the present invention.

As a substance similar to peroxidase, any compounds having a capability equivalent to peroxidase can be used without specific limitation. Examples of such a compound which can be used include cytochrome C, hemoglobin, microperoxidase, and the like.

The quantitative analysis of this invention may be performed through the reaction of the sample to be analyzed, a trivalent cobalt indicator, a divalent cobalt compound, and POD in a buffer solution having a pH of 5 to 10 and maintained at a prescribed temperature (for instance at any temperature between room temperature and 40° C.), followed by the measurement using an optical means of the colored complex produced in the reaction mixture.

The divalent cobalt compound is used at a concentration in the reaction mixture of 0.01 to 10 mmol/l, preferably 0.05 to 1 mmol/l. The trivalent cobalt indicator is used at a concentration in the reaction mixture of 0.01 to 200 mmol/l, preferably 0.05 to 1 mmol/l. POD is used at a concentration in the reaction mixture of 1 to 10,000 U/l, preferably 500 to 5,000 U/l.

Any buffer solution which ca maintain above-mentioned pH can be used without special limitation. Examples of such a buffer solution include acetic acid buffer, phosphoric acid buffer, boric acid buffer, Tris buffer, glycine buffer, Good's buffer, and the like.

In order to determine the amount of hydrogen peroxide, the change in the absorbance is first measured at a wavelength appropriate to the color produced. Alternatively, the absorbance at the same wavelength is measured after a prescribed period of time upon termination of reaction by the addition of an acid, an alkali, or a surface active agent. Then, the value obtained by subtracting the absorbance of the blank sample from the absorbance measured, or said change in the absorbance, is compared with the absorbance or the change in the absorbance of the standard liquid to determine the amount of hydrogen peroxide contained in the sample.

The quantitative analysis of this invention can be applicable to the reaction wherein hydrogen peroxide is produced in the reaction mixture, for instance, to the determination of the amount of hydrogen peroxide produced in a variety of reactions wherein an oxidoreductase is involved. This enables enzymes and their substrates to be quantitatively analyzed. Some of the examples are as follows:

(1) Analysis of a body fluid component (uric acid) using oxidase.

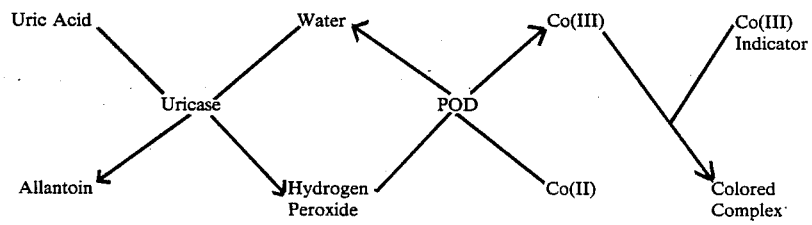

(2) Analysis of a body fluid component (bile acid) using reductase.

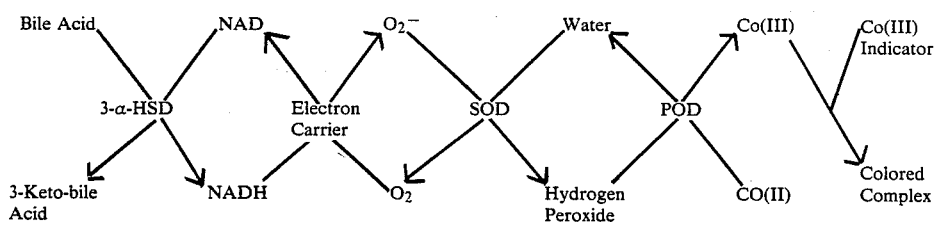

3-α-HSD: 3-α-hydroxysteroid dehydrogenase
NAD: nicotinamide adenine dinucleotide NADH: hydro-form nicotinamide adenine dinucleotide
SOD: superoxide dismutase (3) Analysis of a body fluid component (cholesterol) using dehydrogenase.

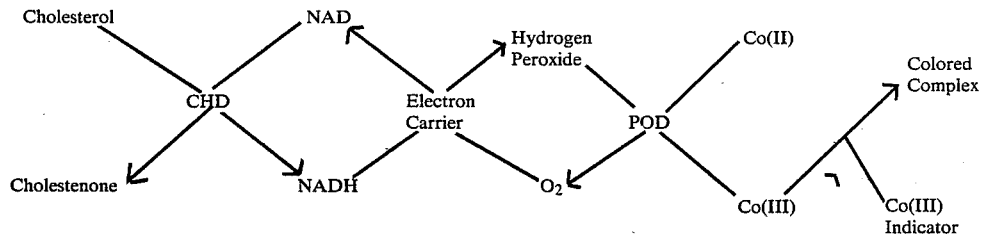

CHD: cholesterol dehydrogenase

It is also possible to quantitatively analyze POD by the use of a reagent containing a divalent cobalt compound, a trivalent cobalt indicator, and hydrogen peroxide.

According to the method of the present invention hydrogen peroxide can be quantitatively analyzed at an extremely high precision. In addition, the method enables various enzymatic activities producing hydrogen peroxide by the reaction with substrates as well as the amount or activity of substances (substrates) involving the known enzymatic reactions linked with such enzymatic reactions, of enzymes and coenzymes to be quantitatively determined very easily at a high sensitivity at a wavelength of above 600 nm without the interference of hemoglobin, bilirubin, or turbidity.

Other features of the invention will become apparent in the course of the following description of the exemplary embodiments which are given for illustration of the invention and are not intended to be limiting thereof.

EXAMPLES

Reference Example 1

Synthesis of TASBB (Compound 14)

Into 12 ml of water 0.756 g of m-aminobenzoic acid was suspended. To the suspension 0.795 g of sodium carbonate was added and the mixture was heated at 95° C. Then, 1.83 g of butane sultone was added dropwise while stirring. To this mixture was further added 1.06 g of sodium carbonate, 2.44 g of butane sultone, and subsequently 0.4 g of sodium hydroxide. After heating the reaction mixture for 30 minutes while stirring, hydrochloric acid was added to adjust the pH of the mixture at 4. This mixture is herein designated as "Reaction Mixture A".

Separately, a solution was prepared by dissolving 0.746 g of 2-aminothiazole sulfate into 3 ml of 3 N hydrochloric acid aqueous solution, and adding to this solution 0.345 g of sodium nitrite bit at a time under ice-cooling, followed by further addition of one spoonful of sulfamic acid using a spatula. This solution was added dropwise to Reaction Mixture A under ice-cooling. The mixture turned deep purple. This was condensed to dryness and the target compound was separated from the residue by means of a reversed ODS column. The crude crystals were dissolved into methanol, and to the solution was added acetone to recrystalize pure Compound 14 as red crystals

| Elemental Analysis: as $C_{18}H_{21}N_4O_8S_3Na_3 \cdot H_2O$ | | | |
|---|---|---|---|
| Calculated: | C: 35.76% | H: 3.83% | N: 9.26% |
| Found: | C: 36.04% | H: 3.89% | N: 9.21% |

EXAMPLE 1

Quantitative analysis of hydrogen peroxide

Into 1 ml of 50 mmol/l phosphate buffer (pH 7.0) containing 0.025 mmol/l cobalt(II) ammonium sulfate, 0.04 mmol/l TASBB, and 2,000 U/l peroxidase, was added 10 μl of sample containing hydrogen peroxide. After heating the mixture at 37° C. for 5 minutes, the absorbance at a wavelength of 678 nm was measured, with a blank sample being used as a control. The results are shown in Table 1.

TABLE 1

| Hydrogen Peroxide Concentration (μmol/l) | Absorbance |
|---|---|
| 50 | 0.127 |
| 100 | 0.254 |
| 150 | 0.382 |
| 200 | 0.508 |

The calibration curve was a straight line passing through the origin.

EXAMPLE 2

Quantitative analysis of hydrogen peroxide

Into 3 ml of 20 mmol/l phosphate buffer (pH 5.0) containing 0.1 mmol/bis(acetylacetonato) cobalt(II), 0.07 mmol/l TAMSMB, and 1,000 U/l peroxidase, was added 20 μl of sample containing hydrogen peroxide. After heating the mixture at 37° C. for 5 minutes, the absorbance at a wavelength of 655 nm was measured, with a blank sample being used as a control. The results are shown in Table 2.

TABLE 2

| Hydrogen Peroxide Concentration (μmol/l) | Absorbance |
|---|---|
| 10 | 0.124 |
| 25 | 0.309 |
| 50 | 0.618 |
| 75 | 0.928 |
| 100 | 1.236 |

The calibration curve was straight line passing through the origin.

EXAMPLE 3

Quantitative analysis of glucose

Into 1.0 ml of 50 mmol/l phosphate buffer (pH 7.0) containing 0.05 mmol/l cobalt(II) ammonium sulfate, 0.04 mmol/l TASBB, and 2,000 U/l peroxidase, was added 10 μl of sample containing glucose. After heating the mixture at 37° C. for 5 minutes, the absorbance at a wavelength of 678 nm was measured, with a blank sample being used as a control. The results are shown in Table 3.

TABLE 3

| Glucose Concentration (μmol/l) | Absorbance |
| --- | --- |
| 50 | 0.074 |
| 100 | 0.149 |
| 200 | 0.297 |
| 300 | 0.445 |
| 400 | 0.593 |
| 500 | 0.742 |

The calibration curve was a straight line passing through the origin, exhibiting a good quantitative measurement.

EXAMPLE 4

Quantitative analysis of uric acid

Into 10 μl of a sample containing uric acid 0.5 ml of 50 mmol/l phosphate buffer (pH 6.5) containing 0.08 mmol/l TASBB and 200 U/l uricase was added. After heating the mixture at 37° C. for 5 minutes, 0.5 ml of 50 mmol/1 phosphate buffer (pH 6.5) containing 0.1 mmol/1 cobalt(II) nitrate and 4,000 U/l peroxidase was added. The mixture was heated at 37° C. for another 5 minutes and the absorbance at a wavelength of 678 nm was measured, with a blank sample being used as a control. The results are shown in Table 4.

TABLE 4

| Uric Acid Concentration (mg/dl) | Absorbance |
| --- | --- |
| 2.5 | 0.319 |
| 5.0 | 0.639 |
| 7.5 | 0.958 |
| 10.0 | 1.277 |

EXAMPLE 5

Comparison of Sensitivity and Maximum Absorbance Wavelength

Into 1.0 ml of 50 mmol/l phosphate buffer (pH 6.5) containing 0.03 wt % 4-aminoantipyrine, 0.02 wt % phenol, and 2,000 U/l peroxidase, was added 10 μl of sample containing hydrogen peroxide. After heating the mixture at 37° C. for 5 minutes, the absorbance at a wavelength of 505 nm was measured, with a blank sample being used as a control.

Quantitative analysis was conducted in the same manner as in Example 1 using several different types of trivalent cobalt indicators. Relative sensitivities with the use of these types of indicators were determined taking the sensitivity of the above measurement as 1. The wavelengths at the maximum absorbance were also determined with respect to these indicators. The results are shown in Table 5.

TABLE 5

| Indicator | Relative Sensitivity | Maximum Absorbance (nm) |
| --- | --- | --- |
| 4-aminiantipyrine and phenol | 1 | 505 |
| TASBB | 65 | 673 |
| TAMSMB | 51 | 654 |
| BTAMB | 27 | 680 |
| PAMB | 42 | 665 |

Example 6

Quantitative analysis of peroxidase

Into 100 μl of a sample containing peroxidase 1.0 ml of 30 mmol/l phosphate buffer (pH 4.0) containing 0.06 mmol/l TAMSMB, 0.06 mmol/l cobalt (II) nitrate, and 0.625 mmol/l of hydrogen peroxide was added. After heating the mixture at 37° C. for 5 minutes, the absorbance at a wavelength of 654 nm was measured, with a blank sample being used as a control. The results are shown in Table 6.

TABLE 6

| Peroxidase Concentration (U/ml) | Absorbance |
| --- | --- |
| 0.10 | 0.195 |
| 0.25 | 0.488 |
| 0.50 | 0.975 |
| 0.75 | 1.463 |
| 1.00 | 1.951 |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A method for quantitative analysis of hydrogen peroxide which comprises:

reacting a divalent cobalt compound with hydrogen peroxide in the presence of an oxidant selected from the group consisting of peroxidase, cytocrome C, hemoglobin and microperoxidase to produce a trivalent cobalt compound, reacting the trivalent cobalt compound thus produced with a trivalent cobalt indicator to produce a colored complex, and subjecting the colored complex to colorimetric quantitative analysis.

2. The method according to claim 1, wherein said trivalent cobalt indicator is a compound represented by the following formula (I) or a salt thereof:

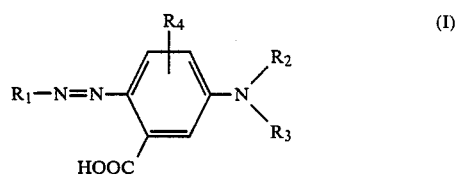

wherein $R_1$ represents

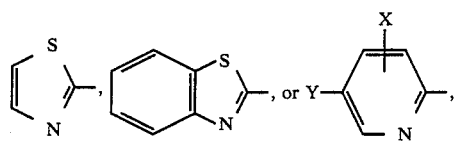, or 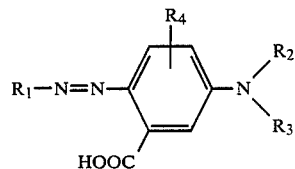

(wherein X and Y may be the same or different and represent hydrogen atoms, halogen atoms, or halogenated alkyl groups), wherein $R_2$ and $R_3$ may be the same or different and represent hydrogen atoms, lower alkyl groups, sulfo alkyl groups, or ω-sulfohydroxy alkyl groups, and $R_4$ represents a hydrogen atom or a lower alkyl group.

3. A reagent for quantitative analysis of hydrogen peroxide which comprises a divalent cobalt compound, a trivalent cobalt indicator, and an oxidant selected from the group consisting of peroxidase, cytocrome C, hemoglobin and microperoxidase.

4. A reagent according to claim 3, wherein said trivalent cobalt indicator is a compound represented by the following formula (I) or a salt thereof:

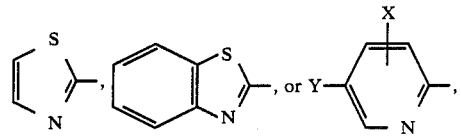

wherein $R_1$ represents

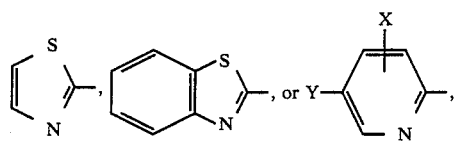, or 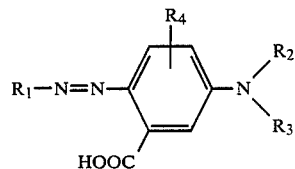

(wherein X and Y may be the same or different and represent hydrogen atoms, halogen atoms, or halogenated alkyl groups), wherein $R_2$ and $R_3$ may be the same or different and represent hydrogen atoms, lower alkyl groups, sulfo alkyl groups, or ω-sulfohydroxy alkyl groups, and $R_4$ represents a hydrogen atom or a lower alkyl group.

* * * * *